United States Patent
Bernard et al.

(10) Patent No.: US 7,875,693 B2
(45) Date of Patent: Jan. 25, 2011

(54) SYNTHESIS OF BIURETS AND ISOCYANATES WITH ALKOXYSILANE FUNCTIONS, FORMULATIONS CONTAINING SAME AND USE THEREOF

(75) Inventors: Jean-Marie Bernard, Saint Laurent d'Agny (FR); Johannes Schwarz, Lyons (FR); Denis Revelant, Genas (FR)

(73) Assignee: Perstorp France, Saint Priest (FR)

( * ) Notice: Subject to any disclaimer, the term of this patent is extended or adjusted under 35 U.S.C. 154(b) by 0 days.

(21) Appl. No.: 10/579,808

(22) PCT Filed: Dec. 16, 2004

(86) PCT No.: PCT/FR2004/003261

§ 371 (c)(1),
(2), (4) Date: May 16, 2006

(87) PCT Pub. No.: WO2005/070942

PCT Pub. Date: Aug. 4, 2005

(65) Prior Publication Data
US 2007/0015895 A1    Jan. 18, 2007

(30) Foreign Application Priority Data
Dec. 24, 2003   (FR) ................... 03 15410

(51) Int. Cl.
| *C07C 273/00* | (2006.01) |
| *C07C 275/00* | (2006.01) |
| *C08G 18/08* | (2006.01) |
| *C08G 18/28* | (2006.01) |
| *C08G 77/04* | (2006.01) |
| *C08G 77/26* | (2006.01) |
| *C08L 75/00* | (2006.01) |
| *C08L 83/00* | (2006.01) |
| *C08L 83/04* | (2006.01) |

(52) U.S. Cl. .................. 528/28; 524/588; 524/589; 524/590; 528/38; 560/335

(58) Field of Classification Search ................. 524/588, 524/589, 590; 528/28, 38; 560/335
See application file for complete search history.

(56) References Cited

U.S. PATENT DOCUMENTS

| 3,361,783 | A |   | 1/1968 | Fink |
| 3,903,052 | A | * | 9/1975 | Wagner et al. ............. 528/21 |
| 3,933,756 | A |   | 1/1976 | Wagner |
| 4,143,060 | A |   | 3/1979 | Wagner et al. |
| 4,412,073 | A |   | 10/1983 | Robin |
| 4,512,898 | A |   | 4/1985 | Oi et al. |
| 2001/0031848 | A1 |   | 10/2001 | Windmueller et al. |
| 2003/0096909 | A1 |   | 5/2003 | Bernard et al. |
| 2003/0135007 | A1 |   | 7/2003 | Ewald et al. |

FOREIGN PATENT DOCUMENTS

| EP | 0 649 850 | A1 |   | 4/1995 |
| EP | 0 765 893 | A1 |   | 4/1997 |
| EP | 1 318 160 | A1 |   | 6/2003 |
| JP | 62-250021 | A | * | 10/1987 |
| WO | WO 02/077057 | A1 |   | 10/2002 |

OTHER PUBLICATIONS

International Search Report for PCT/FR2004/003261.

* cited by examiner

*Primary Examiner*—Patrick D Niland
(74) *Attorney, Agent, or Firm*—Buchanan Ingersoll & Rooney P.C.

(57) ABSTRACT

The invention relates to a composition and a method of preparing one such composition and an isocyanatoalkoxysilane; the polyisocyanate composition contains at least two different oligomeric compounds comprising at least three units and at most five units selected from aminoalkylsilane units and diamine units and at least one function selected from isocyanate functions and from those derived therefrom, the aforementioned compounds having at least two aminoalkylsilane units and another compound having at least two diamine units; the invention is suitable for coatings.

5 Claims, 2 Drawing Sheets

SYNTHESIS OF BIURETS AND ISOCYANATES WITH ALKOXYSILANE FUNCTIONS, FORMULATIONS CONTAINING SAME AND USE THEREOF

This application is an application under 35 U.S.C. Section 371 of International Application Number PCT/FR2004/003261 filed on Dec. 16, 2004.

A subject matter of the present invention is polyisocyanate compositions exhibiting silane functional groups and in particular alkoxysilane functional groups, the preparation of these compositions and the use of these compositions. Another subject matter of the invention is the synthesis of monomers comprising both a silane functional group and an isocyanate functional group.

In order to place the present invention in industrial and semantic context, it is advisable to restate a certain number of points and to specify or recall a certain number of definitions.

Predominantly, polyisocyanate compositions are generally formed from derivatives resulting from the oligocondensation of individual di-, tri-, indeed even tetraisocyanate molecule(s).

Such a type of molecule is described as "monomers" and is capable of being obtained by phosgenation of a di(primary amine), optionally carrying one, indeed even two, other primary amine functional groups. Thus, such a molecule comprises a unit composed of a carbon chain carrying at least two nitrogens (originating from the diamine to be phosgenated), which unit will be denoted by "diamino unit" in the continuation of the description. The diamino unit serves here as vestiges or mark of the existence, past or present, of an isocyanate monomer: thus, the diamino unit has the structure

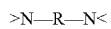

where R represents a hydrocarbon radical which is the residue of an isocyanate monomer, after ignoring two isocyanate functional groups. Of course, R does not exhibit any of the functional groups created during oligomerization of an isocyanate functional group, namely the carbamate, urea (including biuret), allophanate or biuret functional groups and those which are mentioned on the occasion of the description of the oligocondensation (including oligomerization). The molecular weight of —R— is at most equal to 200. R can comprise another "amino" group in the case of the trifunctional monomers, such as LTI, NTI and UTI.

The "amino" symbols N< and >N mean that the nitrogen can be inserted into any functional group, such as isocyanate, amine, amide, imide or urea functional group, and in particular the functional groups generated by the oligomerization reactions.

These diamino units are found in virtually all of the oligocondensations and in the vast majority of the conversions of the isocyanate functional groups. This observation makes it possible to refer to the number of diamino units in order to indicate in particular the state of condensation of the oligocondensates (including oligomers), indeed even of the polycondensates, and even in the case of heterocondensates (in which cases, it is possible to have several types of diamino units).

According to the usage common in chemistry, when a functional group has given its name to a family of compounds, as is the case for the isocyanates, the aromatic or aliphatic nature is defined according to the point of attachment of the functional group under consideration. When an isocyanate is situated on a carbon of aliphatic nature, then the isocyanate compound is itself considered to be of aliphatic nature. Likewise, when an isocyanate functional group is attached to the backbone via a carbon of aromatic nature, then the whole monomer will be denoted by the expression "aromatic isocyanate".

To clarify this point, it may be restated that:
  any isocyanate functional group having a point of attachment which is a member of an aromatic ring is regarded as aromatic;
  any isocyanate functional group having a point of attachment (of the nitrogen, of course) which is a carbon of $sp^3$ hybridization is regarded as aliphatic.

The following distinctions may be made among aliphatic isocyanates:
  Any aliphatic isocyanate functional group having a point of attachment separated from the closest ring by at most one carbon (it is even preferably directly connected to it) is regarded as cycloaliphatic.
  Any isocyanate functional group having a point of attachment carried by a secondary $sp^3$ carbon (that is to say, a carbon connected to two carbons and to a hydrogen) is regarded as secondary.
  Any isocyanate functional group having a point of attachment carried by a tertiary $sp^3$ carbon (that is to say, a carbon connected to three carbons) is regarded as tertiary.
  Any isocyanate functional group having a point of attachment carried by an $sp^3$ carbon itself carried by a tertiary carbon (that is to say, not taking into account the final bond, a carbon connected to three carbons) is regarded as neopentylic.
  Any isocyanate functional group having a point of attachment carried by a methylene sensu stricto (—$CH_2$—) itself carried by an exocyclic and nontertiary $sp^3$ carbon is regarded as linear.

Figure 1:
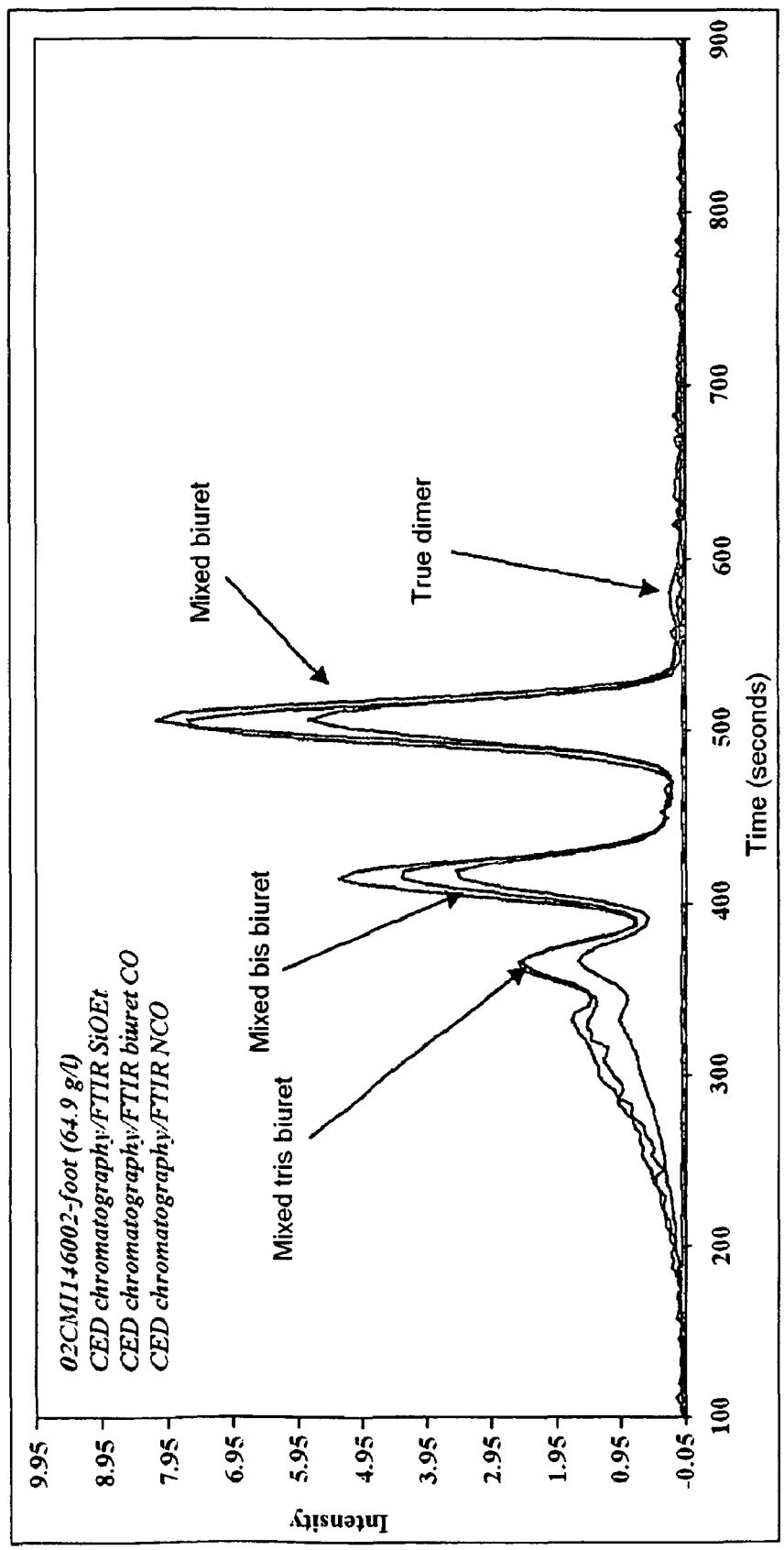
FIG. 1 is a chromatogram showing the distribution of the oligomers in Example 5.
Figure 2:
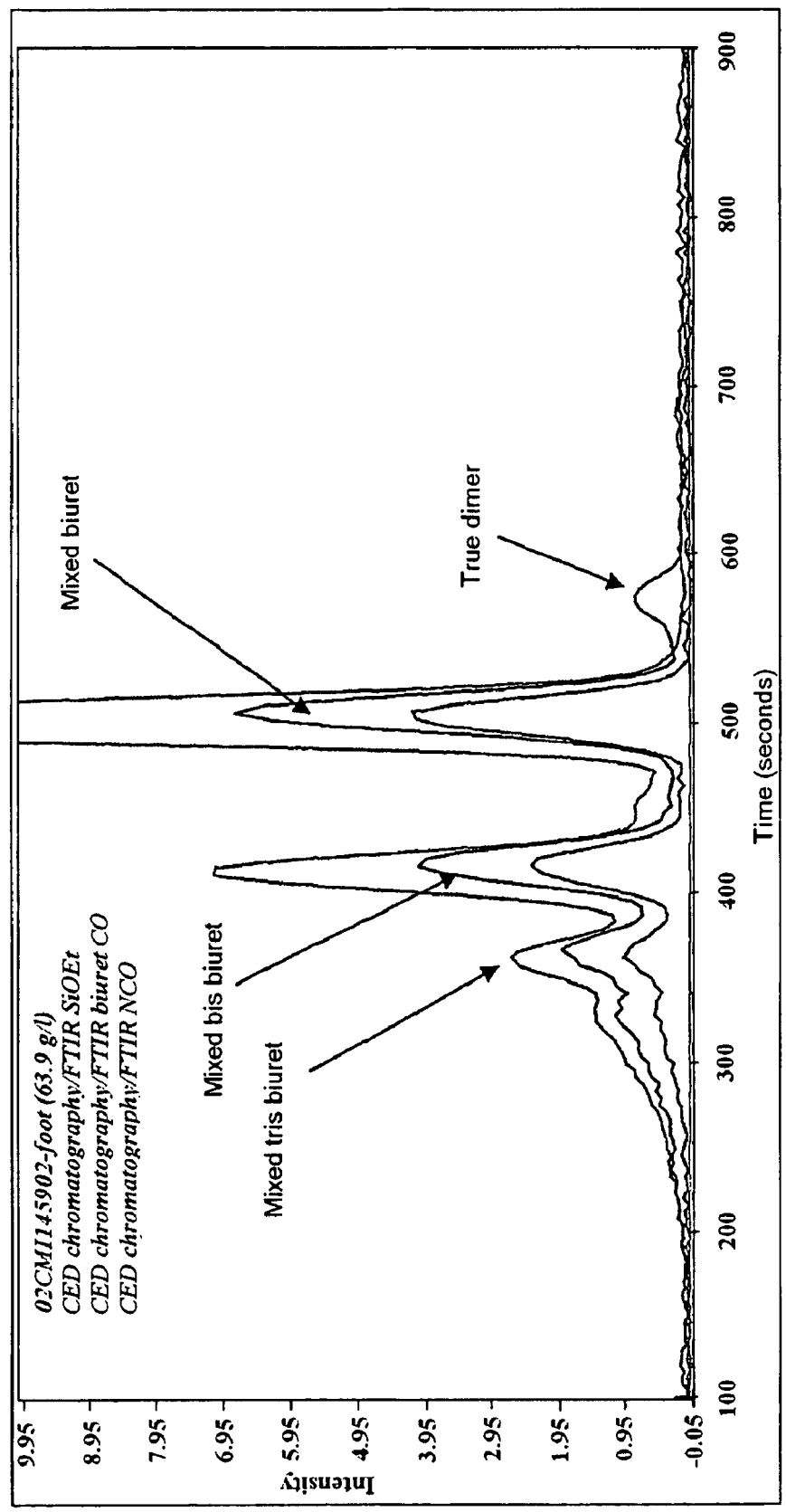
FIG. 2 is a chromatogram showing the distribution of the oligomers in Example 6.

As regards the monomers and for the present description:
  "aliphatic" is understood to mean any monomer, all the isocyanate functional groups of which are aliphatic;
  "aromatic" is understood to mean any monomer, all the isocyanate functional groups of which are aromatic;
  "mixed" is understood to mean any monomer, one functional group at least of which is aliphatic and one functional group at least of which is aromatic;
  "cycloaliphatic" is understood to mean any monomer, all the isocyanate functional groups of which are aliphatic and one at least of which is cycloaliphatic;
  "linear aliphatic" is understood to mean any monomer, all the isocyanate functional groups of which are aliphatic, none of which are cycloaliphatic and one at least of which is linear, or which exhibits at least one polymethylene sequence, free in rotation and thus exocyclic, $(CH_2)_\pi$ where $\pi$ represents an integer at least equal to two.

To explain in a little more detail, the isocyanate monomers can be:
  aliphatic, including cycloaliphatic and arylaliphatic (or araliphatic), such as:
    as linear (or simple) aliphatic, polymethylene diisocyanate monomers which exhibit one or more exocyclic polymethylene sequences $(CH_2)_\pi$ where $\pi$ represents an integer from 2 to 10, advantageously from 4 to 8, and in particular hexamethylene diisocyanate, it being possible for one of the methylenes to be substituted by a methyl or ethyl radical, as is the case with MPDI (methylpentamethylene diisocyanate);

as cyclic aliphatic (or cycloaliphatic): partially "neopentylic" and cycloaliphatic; isophorone diisocyanate (IPDI);

as cyclic aliphatic (cycloaliphatic) diisocyanate, those derived from norbornane or the hydrogenated forms (hydrogenation of the nucleus, resulting in a diaminated ring subsequently subjected to isocyanation, for example by phosgenation) of the aromatic isocyanates;

as araliphatic, arylenedialkylene diisocyanates (such as OCN—CH$_2$-Φ-CH$_2$—NCO; a portion of which is regarded as linear aliphatic, namely those having the isocyanate functional group separated from the aromatic nuclei by at least two carbons, such as (OCN—[CH$_2$]$_t$-Φ-[CH$_2$]$_u$—NCO) with t and u greater than 1;

or also aromatic, such as toluoylene diisocyanate, mentioned here as a matter of interest but the hydrogenated form of which, on the other hand, is regarded as cycloaliphatic and is advantageous, such as 1,3- and 1,4-BIC (BisIsocyanatomethylCyclohexane).

Generally, the molecular weight of a monomer does not exceed 300 and is at least equal to 100.

According to the present invention, it is desirable for linear aliphatic monomers to be used at least partially for the implementation of the present invention. To those which are mentioned above can also be added lysine derivatives and in particular LDI (Lysine DiIsocyanate, resulting from ester of lysine) or LTI (Lysine TriIsocyanate, resulting from the ester of lysine with ethanolamine), NTI (Nonyl TriIsocyanate OCN—(CH$_2$)$_4$—CH(CH$_2$—NCO)—(CH$_2$)$_3$—NCO) or UTI (Undecyl TriIsocyanate OCN—(CH$_2$)$_5$—CH(—NCO)—(CH$_2$)$_5$—NCO).

The majority of these monomers have a vapor pressure which is too high to meet regulatory requirements relating to safety at work. Consequently, these molecules are increased in size by polycondensing them.

These condensations involve the isocyanate functional groups. As the "monomers" are polyfunctional with regard to isocyanate, these condensations can take place on two or more isocyanate functional groups of the same molecule. It follows that these reactions can result in oligomers which are smaller or bigger in size depending on the degree of conversion of the isocyanates.

The main polycondensates will be restated below:

The derivatives obtained by "trimerization", that is to say that three isocyanate functional groups belonging to three different molecules are condensed to form an isocyanuric ring carrying three groups themselves carrying an isocyanate functional group.

The main units, functional groups or rings liable to be formed on the occasion of the trimerization may be restated:

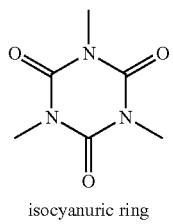
isocyanuric ring

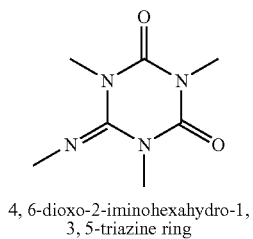
4, 6-dioxo-2-iminohexahydro-1, 3, 5-triazine ring

-continued

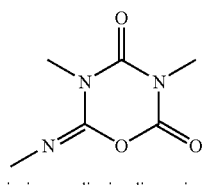
iminooxadiazinedione ring

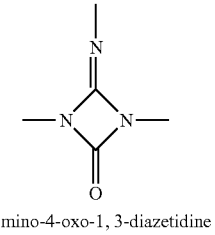
2-imino-4-oxo-1, 3-diazetidine

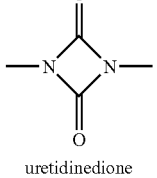
uretidinedione

Another way of increasing the size of the molecule is to condense them with one another in the presence of water to form a derivative carrying three isocyanate functional groups which is denoted under the expression of biuret. The reaction below shows the reaction in the commonest case, that is to say the case where the three molecules to be condensed are the same:

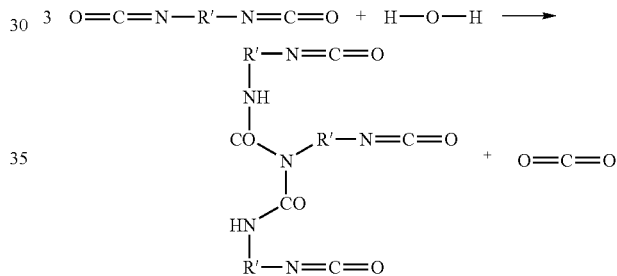

It is also possible to condense these monomers with alcohols, in particular polyols, which gives carbamate and then allophanate polyfunctional compounds.

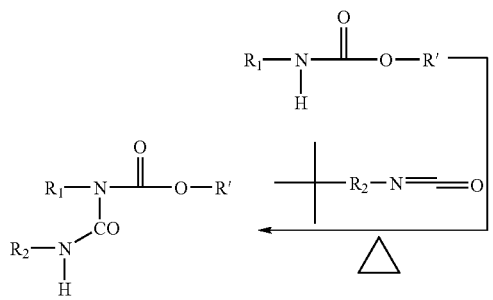

In the polyisocyanate compositions, in addition to the predominant polycondensates, more often than not minor amounts of various condensation types are encountered.

The great majority of isocyanates were until recently essentially dissolved in organic solvents. The use of organic solvents is increasingly often subject to criticism by the authorities in charge of safety at work as these solvents, or at least some of them, are supposed to be toxic or chronically toxic. This is the reason why attempts are increasingly being made to develop technologies which comprise only a very small amount of solvent, indeed which are even devoid of solvent.

In particular, in order to reduce the use of organic solvent, the presence of which is supposed to be toxic to those who handle it and harmful to the environment, the proposal has been made to develop isocyanate compositions which are less viscous. This lowering in viscosity makes it possible to reduce the amount of solvent and renders the compositions more capable of being emulsified.

Furthermore, the market is demanding a compound which makes it possible to carry out a twofold crosslinking and thus to produce a twofold or multiple functionality.

In addition, a search is always underway for compositions which make possible strong adhesion, with or without primer, or which are even capable of acting as primer.

A search is thus underway for an adhesion promoter.

Mention may in particular be made, among the most widely used oligomeric polyisocyanate compositions, of the oligomer mixture exhibiting a biuret unit and familiarly denoted by "biuret".

This biuret is currently produced by the action of water on isocyanate monomers in the presence of a very small amount of acid.

The degree of conversion of the monomer is of the order of 45%.

In the case where the monomer is hexamethylene diisocyanate, the viscosity of the product resulting from the synthesis after distillation of the monomer is of the order of 9000 mPa·s.

There are two significant disadvantages to this synthesis: the formation of insoluble ureides, which it is advisable to remove, and, on the other hand, the relatively high viscosity of the product after distillation of the monomer.

Generally, ureas often exhibit problems of insolubility, in particular with regard to compounds with a markedly lipophilic nature.

Furthermore, the market requires compositions exhibiting a high functionality.

Furthermore, a few isocyanate monomers comprising an alkoxysilane functional group are known. Mention may be made, by way of examples, of isocyanatopropyltrimethoxysilane and isocyanatopropyltriethoxysilane. These volatile monomers are classified as toxic.

Polyisocyanates comprising alkoxysilane functional groups are regarded as difficult to access, in particular when a high content of alkoxysilane groups is desired. They are generally obtained by grafting alkoxysilane molecules comprising a mobile hydrogen functional group to the isocyanate functional groups of a polyisocyanate. Generally, the alkoxysilane molecules used are amines which, by reaction with the isocyanate functional groups of a polyisocyanate, give alkoxysilane polyureas which are generally solid and not very soluble in organic solvents. These compounds do not give homogeneous mixtures.

This low solubility in organic solvents has led users to graft only a portion of the isocyanate functional groups and to obtain alkoxysilane urea isocyanate hybrid compounds.

However, this partial grafting solution is not always advantageous as the control of the grafting is not easy and depends on the structures of the polyisocyanates used, and in particular nonspontaneous crystallization phenomena occur, resulting in crystallization of the alkoxysilane urea polyisocyanates during the storage of formulations comprising these derivatives.

Furthermore, these alkoxysilane urea structures bring about increases in the viscosity of the formulations and thus require larger volumes of solvent in order to be able to be applied correctly. This increase in solvents is not or not very compatible with the step of reducing volatile organic discharges to the atmosphere.

This is why one of the aims of the present invention is to provide a process which reduces or eliminates the formation of insoluble ureides.

Another aim of the present invention is to provide a technology which makes it possible to render compatible isocyanate and silane and in particular alkoxysilanes.

Another aim of the present invention is to provide isocyanate compositions in which the isocyanate comprises a biuret group.

Another aim of the present invention is to provide a process which makes it possible to reduce the viscosity of the final composition for the same degree of conversion of the monomer(s), the measurement of the viscosity being carried out under "standard" conditions, after removal of the residual monomer(s) (the compositions targeted exhibit, by weight, at most 1%, advantageously at most 0.5%, preferably at most 0.2%, more preferably at most 0.1%). For the measurement of the viscosity, see Standard NFT 30-029 (October 1980).

Another aim of the present invention is to provide compositions comprising a biuret group which exhibit a reduced viscosity.

Another aim of the present invention is to provide polyisocyanate compositions of high functionality which can be used alone or as a mixture with others.

Another aim of the present invention is to provide polyisocyanate compositions having a twofold or multiple functionality which makes it possible to carry out a twofold crosslinking.

Another aim of the present invention is to provide polyisocyanate compositions a strong adhesion, with or without primer, or which are even capable of acting as primer.

These aims and others which will become apparent subsequently are achieved by means of a composition comprising at least two distinct oligomeric compounds comprising at least three units and at most 5 (to limit perhaps at 4) units chosen from aminoalkylsilane units and diamino units and at least one functional group chosen from isocyanate functional groups and from those which derive therefrom, characterized in that one of said compounds comprises at least two aminoalkylsilane units and in that another comprises at least two diamino units.

Advantageously, these compositions do not comprise monomer; see above with regard to the measurement of the viscosity.

In said composition, it is desirable for there to be as little true urea functional group as possible; advantageously, the ratio of the true urea functional groups (numerator) to the acylurea and biuret functional groups (denominator) is at most equal to 1/2, advantageously to 1/3, preferably to 1/5, more preferably to 1/10. Such ratios are readily accessible by spectroscopic measurements.

When there is no biuret or acylurea, the content of true urea functional group is advantageously at most equal to 1% of the isocyanate (NCO) functional groups, preferably to 0.5%.

The following unit is regarded as true urea functional group:

—NH—CO—N<, in which the bonds of the nitrogens left open are connected only to hydrogen and/or to an aliphatic radical.

It is desirable, with regard to the combined composition, for the ratio in equivalents of the aminoalkylsilane units to the diamino units to be at least equal to 15%.

Generally, said oligomeric compounds each represent at least 3%, advantageously at least 5%, preferably at least 8%, by weight of the composition.

Furthermore, it is desirable for said oligomeric compounds to represent, for each category, at most 2/3, advantageously, preferably 1/3, by weight of the composition.

According to a preferred implementation of the present invention composition as claimed in claims 1 to 4, characterized in that, with regard to the combined oligomeric compounds (that is to say, oligomeric compounds comprising at least three units and at most 5 units chosen from aminoalkylsilane units and diamino units and at least one functional group chosen from isocyanate functional groups and from those which derive therefrom), the compounds in which the aminoalkylsilane units represent at least two fifths of the units under consideration (aminoalkylsilane units and diamino units) form at least 1/5 of the mixture.

said functional groups which derive from the isocyanate functional groups are advantageously chosen from the carbamate, uretidinedione, isocyanurate, biuret, allophanate, pseudoallophanate, 4,6-dioxo-2-iminohexahydro-1,3,5-triazine, iminooxadiazinedione and 2-imino-4-oxo-1,3-diazetidine functional groups.

composition as claimed in claims 1 to 6, characterized in that said aminoalkylsilane unit corresponds to the formula (I):

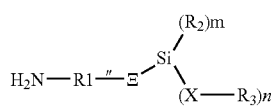

where $\Xi$ represents either a single bond or a chalcogen, preferably an oxygen.

Advantageously, said compounds are compounds comprising a biuret functional group.

Advantageously, the composition exhibits a content of biuret functional group (>N—CO—N(-)—CO—N<, MW=84) at least equal to 5%, advantageously to 8%, preferably to 10%. This content of biuret functional group (>N—CO—N(-)—CO—N<, MW=84) is at most equal to 20%, advantageously to 18%, preferably to 16%.

The composition exhibits a total content of isocyanate functional group (free and blocked) at least equal to 5%, advantageously to 8%, preferably to 10%, more preferably to 12%.

According to one implementation of the present invention, the composition exhibits a content of free isocyanate functional group at least equal to 5%, advantageously to 8%, preferably to 10%, more preferably to 12%.

According to one implementation of the present invention, the composition exhibits a content of blocked isocyanate functional group at least equal to 5%, advantageously to 8%, preferably to 10%, more preferably to 12%.

According to the present invention, the composition (with unblocked isocyanate functional groups) can exhibit a viscosity at most equal to 6000 mPa·s, advantageously to 4000 mPa·s, preferably to 3000 mPa·s, which is remarkable for biuret-based polyisocyanate compositions.

The composition comprises at most 2%, advantageously at most 1%, preferably at most 0.5%, by weight of isocyanate monomer(s) (generally diisocyanatoalkane).

Furthermore, according to an advantageous embodiment of the invention, the composition can comprise at most 2%, advantageously at most 1%, preferably at most 0.5%, by weight of isocyanatoalkylsilane (corresponding to the aminoalkylsilane).

Another aim of the present invention is to provide a process for the preparation of an isocyanate composition comprising biuret functional groups, characterized in that at least one isocyanate monomer is brought into contact with an aminoalkylsilane (or silanoalkylamine) so that an isocyanatoalkylsilane is formed.

The process is based on the result of the study of the equilibria set out below. This process makes it possible to prepare biuret without the addition of water and while producing, as potential by-product, an isocyanatosilyl derivative (isocyanatoalkoxysilane) which is difficult to manufacture (see above), in particular of formula Ib

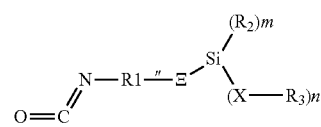

The reaction with the amine begins as follows:

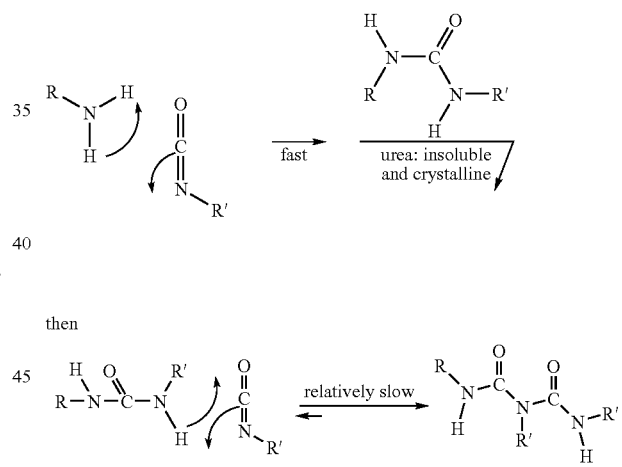

where R represents an amine-carrying radical and in particular

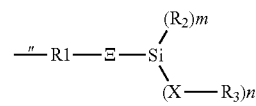

where R' represents the residue of an isocyanate after ignoring one isocyanate functional group.

However, the reversible formation of the biuret can result in the formation of the isocyanate on the radical of the amine if the reaction mixture is heated sufficiently for a long enough period of time:

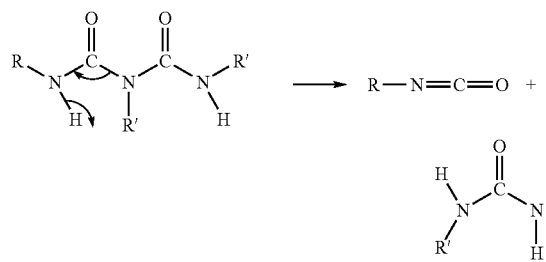

This reaction, which is promoted by the relative volatility of the silyl radical, makes it possible to obtain all the alternative forms of the biuret, if the reaction is carried out at reflux, or the isocyanate instead of the starting amine functional group, if the R—NCO formed is distilled off.

This equilibrating of the composition via the exchange with the free monomers results in the formation (with respect to the combined biuret functional groups) of at least 5%, advantageously 7%, preferably 10%, of biuret functional groups which do not carry a silanoalkyl chain. This stabilizes the composition, rendering it more homogeneous.

In order for this equilibrating to take place under satisfactory conditions, it is desirable for the ratio, expressed in equivalents, of the isocyanate functional groups to the number of hydrogens carried by the amine functional groups to be at least 4, advantageously at least 6, preferably at least eight.

It is also desirable to be positioned at a high temperature of at least 140° C., advantageously 150° C., preferably at 160° C., and/or to use biuretization catalysts, such as strong and/or moderate acids.

More specifically, the present invention comprises the preparation of polyisocyanate compositions, the polyisocyanates comprising acyl or carbamoyl urea units and comprising at least one $(R_3—X)_{3-m}Si(R_2)_m$— unit, obtained according to a process which employs a compound comprising at least one isocyanate functional group, preferably at least two isocyanate functional groups, with a compound comprising at least one primary or secondary amine functional group and/or optionally a compound comprising at least one carboxylic acid functional group. The process is characterized by a single-stage reaction with an excess of isocyanate compounds with respect to the amine introduced at a temperature of between 100 and 200° C., preferably between 110° C. and 180° C. The reaction time is between 1 and 10 hours and the excess monomer is subsequently removed by thin film distillation so that the final product comprises a content of HDI monomer of less than 2%, preferably less than 1%.

The degree of conversion of isocyanate is generally set by the amount of amines introduced.

The content of oligomers in the compositions varies with the ratio of isocyanate functional groups to amine functional groups.

Generally, the structures which are subject matters of the invention give relatively low viscosities due to the formation of intramolecular hydrogen bonds in the biuret and/or acylurea units.

Generally, the biuret compositions comprise the structures which can be represented schematically by the following general formula;

$$A\text{-}(NCO)_z—(Si(R_2)_m(X—R_3)_n)_y$$

with

A representing the residue of a backbone comprising biuret and/or acylurea structures;

z representing a number between 0 and 30;

y representing a number between 1 and 30;

m representing an integer within the closed range (that is to say comprising the limits) 0 to 3, advantageously at least equal to 2, preferably to 3;

n representing an integer within the closed range (that is to say comprising the limits) 0 to 3, advantageously at most equal to 2;

with the condition that m+n=3;

$R_2$ representing a linear or branched hydrocarbon chain of 1 to 20 carbon atoms, preferably of 1 to 12 carbon atoms, it being possible for this hydrocarbon chain to be aliphatic, including aralkyl, or aromatic, optionally interrupted by heteroatoms, it being possible for the $R_2$ chain to be of alkylene type if the two terminal carbons of this chain are bonded to the silicon;

$R_3$ representing a linear or branched hydrocarbon chain of 1 to 20 carbon atoms, preferably of 1 to 12 carbon atoms, it being possible for this hydrocarbon chain to be aliphatic or aromatic or aralkyl, optionally interrupted by heteroatoms, it being possible for the $R_3$ chain to be of alkylene type if the two terminal carbons of this chain are bonded to two groups X carried by the same silicon atom;

X=O or S.

Mention may be made, as nonlimiting examples of the general structure, of the following structures:

structures comprising biuret units, hereinafter recorded from 1 to 5 acylurea structures, recorded from 6 to 10

Structure 1: "True" biuret comprising two isocyanate units and one alkoxysilane unit, the amine functional group inserted in the biuret carrying a group Y which can be hydrogen or a linear or branched hydrocarbon chain of 1 to 20 carbon atoms which is aliphatic, including aralphatic, or aromatic, optionally interrupted by heteroatoms.

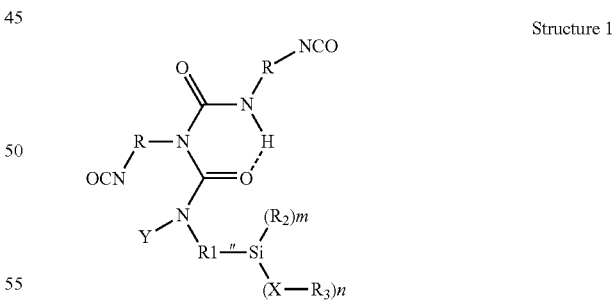

Structure 1

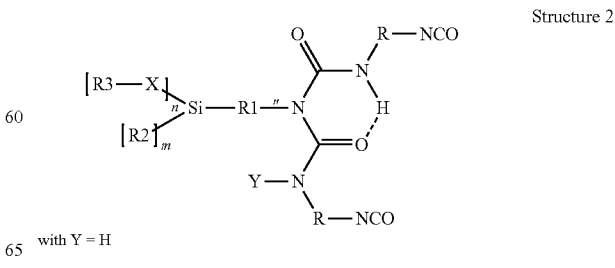

Structure 2 with Y = H with Y representing a hydrogen or a hydrocarbon chain and ⌇ a hydrogen bond Structure 2: "True" biuret comprising two isocyanate units and one alkoxysilane unit, the amine functional group inserted in the biuret carrying a group Y which can only be hydrogen.

Polybiuret structures comprising 2 NCO functionalities: products of the oligomerization of the structures 1 and/or 2 to result in oligomeric sequences comprising from 2 to 20 units. These sequences can be represented schematically as follows, the distribution of the structures being random along the chain.

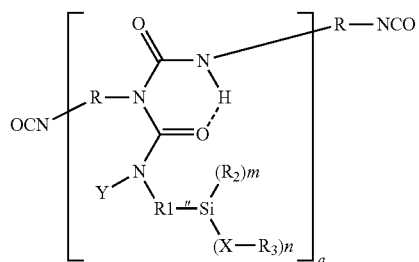

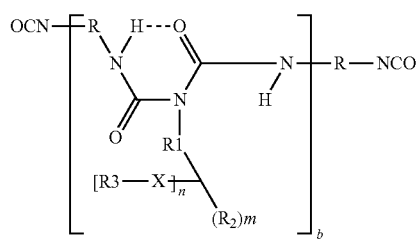

with Y representing a hydrogen or a hydrocarbon chain, ⌇ representing a hydrogen bond and with "a" and "b" representing a value ranging from 2 to 20

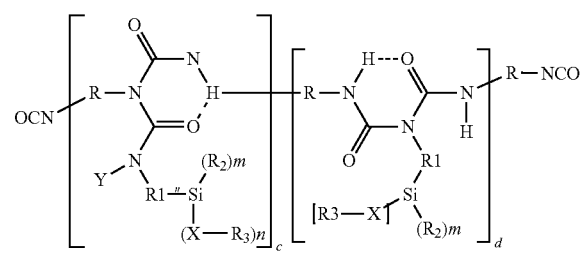

with c + d between 2 and 20

The compositions also comprise biuret structures comprising an isocyanate unit and two alkoxysilane units (structure 3) and much smaller amounts of biuret structures composed of 3 alkoxysilane units (structure 4). The latter structures are only present under certain conditions.

Structure 3 can also be incorporated in polybiuret sequences presented above and, in this case, constitute chain-limiting agents (blocking of the terminal ends of chains) due to their isocyanate monovalency.

The presence of these structures 3 and 4 is explained by the conditions of the process involved and is based on a transisocyanation reaction which can be accelerated by the temperature and by the catalyst selected.

Structure 3: Biuret comprising two alkoxysilane functional groups and one isocyanate unit.

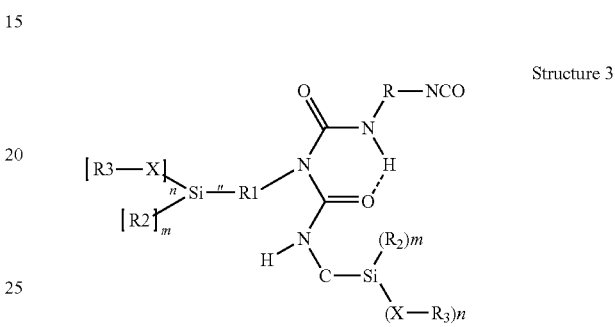

⌇ hydrogen bond

Structure 4: Biuret comprising three alkoxysilane functional groups

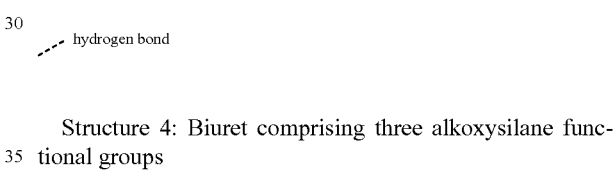

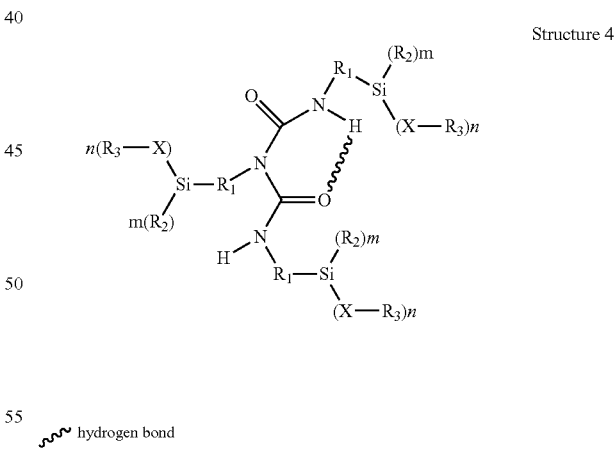

⌇ hydrogen bond

The composition also comprises sequences with a functionality of greater than 2, even if a diisocyanate is used alone in the reaction with a monoaminoalkylsilane. These sequences are the consequence of the process involved.

Structure 5 represents an example of polybiuret sequences with a functionality of greater than 2.

Structure 5: example of polybiuret sequence with a functionality of greater than 2

Structure 5: example of polybiuret sequence with a functionality of greater than 2

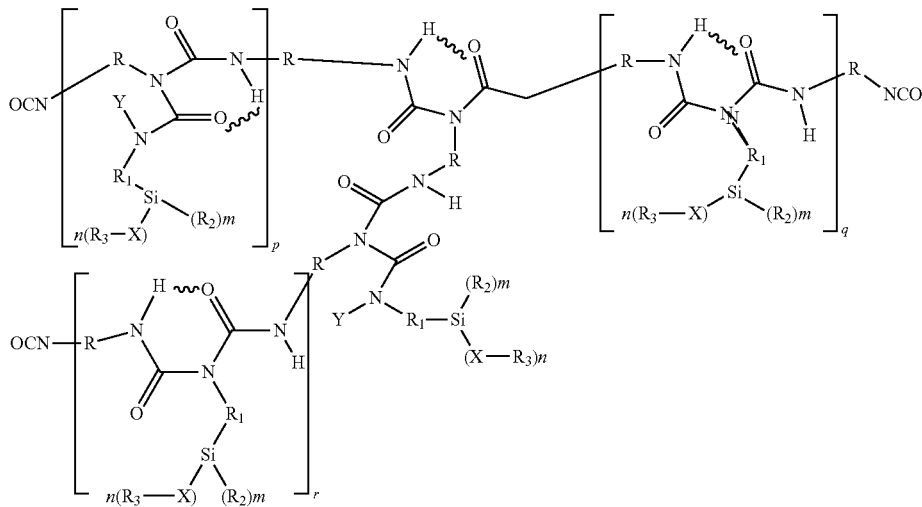

with p + q + r between 3 and 30 with
R the residue of an isocyanate or polyisocyanate molecule carrying at least one isocyanate functional group,
$R_1$ the residue of a molecule carrying at least one silane functional group, generally a linear or branched hydrocarbon chain of 2 to 20 carbon atoms, preferably of 3 to 12 carbon atoms, it being possible for this hydrocarbon chain to be aliphatic or aromatic or aralkyl, optionally interrupted by heteroatoms,
$R_2$ and $R_3$, which are identical or different, defined as above,
n between 1 and 3 and n+m=3,
X=O or S.

Structures Comprising Acylurea Units:

The structures comprising acylurea units can be written as for the biuret structures, except that the $R_4$—C(=O)— unit replaces the R—NH—C(=O)— unit in the biuret structures.

The following acylurea structures 7 to 10 are presented by way of examples. The polyacylurea sequences are not represented but are analogous to the polybiuret sequences.

Acylurea Structures 7 to 9

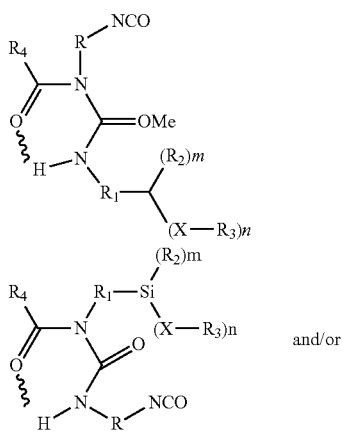

and/or

-continued

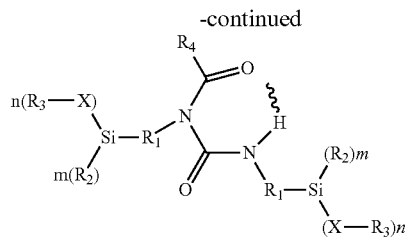

with $\zeta$ hydrogen bond with
$R_4$ representing the residue of a molecule carrying at least one carboxyl functional group which has reacted to give the N-acylurea functional group.

In the case of a diacid ($R_4$—(COOH)$_2$), the acylurea structure then becomes

Structure 10: example of bisacylurea structure comprising alkoxysilane units

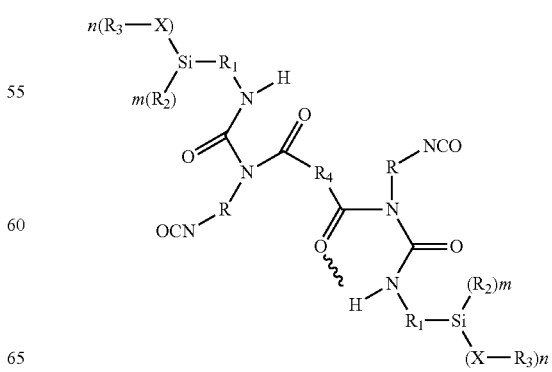

Aside from these structures 1 to 10, the compositions also comprise oligomeric or polymeric molecules comprising sequences comprising the units described above.

The compositions can also comprise structures comprising the following units:

Allophanate: —R—N[—C(=O)—NH—R—NCO]—C(=O)—O—$R_5$

Carbamate: —R—NH—C(=O)—O—$R_5$

Urea: —R—NH—C(=O)—NH—$R_6$— or —R—NH—C(=O)—N—$(R_6)(R_7)$

Uretidinedione:

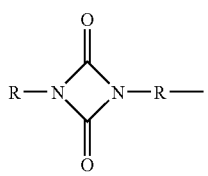

Isocyanurate:

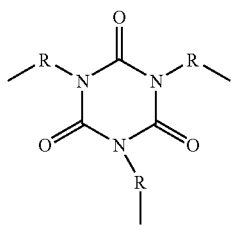

Oxadiazinetrione:

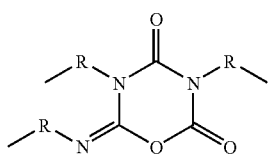

Iminotrimer:

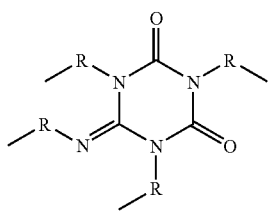

The synthesis of these products comprises the reaction of a compound comprising at least one isocyanate functional group, preferably at least two isocyanate functional groups, with a compound comprising at least one primary and/or secondary amine functional group and at least one alkoxydialkylsilane functional group and/or one alkyldialkoxysilane functional group and/or one trialkoxysilane functional group in the presence optionally of a compound comprising at least one carboxylic acid functional group and of a catalyst. The reaction can be carried out in the presence or in the absence of solvent.

The isocyanate compounds used comprise at least two and at most 10 isocyanate functional groups and preferably at most 4. They can be aliphatic or cycloaliphatic.

Mixtures of polyisocyanate compounds can also be used. In the case of polyisocyanate mixtures, compounds comprising only a single isocyanate functional group per mole of compound can be incorporated but their content of isocyanate functional groups then does not exceed 50 mol %, preferably 25 mol %, of the isocyanate functional groups of the mixture. Polyisocyanate compounds comprising more than 3 isocyanate functional groups and less than 25 can also be incorporated in the mixture but their content of isocyanate functional groups does not exceed 50 mol % of the isocyanate functional groups of the mixture and preferably does not exceed 25 mol %.

Mention may be made, as nonlimiting examples of aliphatic isocyanate compounds, of diisocyanates, such as hexamethylene diisocyanate (HDI), 2-methylpentane diisocyanate (MPDI), dodecane diisocyanate (DDI), or the methyl or ethyl ester or esters of heavier alcohols of lysine diisocyanate (LDI), or triisocyanates, such as the isocyanatoethyl ester of lysine diisocyanate (LTI) or 4-isocyanatomethyl-1,8-octamethylene diisocyanate (TTI).

Mention may be made, as nonlimiting examples of cycloaliphatic isocyanate compounds, of diisocyanates, such as norbornane diisocyanate (NBDI), bis(isocyanatomethyl) cyclohexane (BIC) or isophorone diisocyanate (IPDI).

Mention may be made, as nonlimiting examples of monoisocyanate compounds, of butyl isocyanate, isocyanatopropyltrialkoxysilane or octadecyl isocyanate.

Mention may be made, as nonlimiting examples of polyisocyanate compounds, of the isocyanurate oligomers of HDI or of IPDI.

The compounds carrying at least one primary and/or secondary amine functional group used for the reaction have the following structures:

Y—NH—$R_5$—Si$(R_3$—X$)_{3-m}(R_2)_m$ or

Y—NH—$R_6$—N(—Y)—$R_5$—Si$(R_3$—X$)_{3-m}(R_2)_m$ or $R_6$—[(NH—$R_5$—Si$(R_3$—X$)_{3-m}(R_2)_m$)]$_z$ with Y=H or a linear or branched hydrocarbon chain of 1 to 20 carbon atoms which is aliphatic or aromatic or araliphatic and which is optionally interrupted by heteroatoms, $R_5$ a linear or branched hydrocarbon chain of 1 to 20 carbon atoms which is aliphatic or aromatic or araliphatic and which is optionally interrupted by heteroatoms; $R_5$ is preferably an aliphatic hydrocarbon chain of 1 to 8 carbon atoms, $R_6$ a linear or branched hydrocarbon alkylene chain of 1 to 20 carbon atoms which is aliphatic or aromatic or araliphatic and which is optionally interrupted by heteroatoms, z=2 to 6, preferably z=2.

In the specific case of the preparation of acylureas, it is possible to use all or part of the compounds carrying at least one primary and/or secondary amine functional group and at least one silane functional group in the form of a salt of the compound carrying at least one carboxylic acid functional group.

The compounds carrying at least one carboxylic acid functional group are aliphatic or aromatic or heterocyclic compounds. They comprise at least one carboxylic acid functional group, at most 6, preferably at most 2. The carbon number is between 2 and 20, preferably between 2 and 12.

Mention may be made, as nonlimiting examples of compounds comprising at least one carboxyl functional group, of acetic acid, propionic acid, isobutyric acid, pivalic acid, benzoic acid, 2-ethylhexanoic acid, undecanoic acid, stearic acid and their branched homologs, as nonlimiting examples of compounds comprising at least two carboxyl functional groups, of adipic acid, dodecanedioic acid, undecanedioic acid, glutaric acid and their branched homologs.

The process for the synthesis of the polybiurets comprises:
- introducing an isocyanate, preferably a diisocyanate, or a mixture of isocyanates into a reactor,
- optionally adding a biuretization catalyst, such as a carboxylic acid or a Lewis acid, such as dibutyltin dilaurate,
- heating this mixture of 110° C.,
- adding, to this mixture, a compound carrying at least one primary or secondary amine functional group and carrying a silane functional group, or a mixture of these amines,
- maintaining the reaction medium at a temperature of between 100 and 200° C., preferably between 110° C. and 160° C., for a time of between 1 and 5 hours,
- removing the unreacted monomer by a suitable process, such as vacuum distillation on a thin film device,
- recovering the polybiuret product comprising alkoxysilane units and comprising isocyanate units.

An alternative form of the process comprises adding the amine to the isocyanate under cold conditions and subsequently heating to a temperature of between 100 and 200° C., preferably between 110 and 160° C., for a time of between 1 and 5 hours.

Another alternative form of the process comprises adding the isocyanate to the amine or to the mixture of amines comprising silane functional groups and raising the reaction temperature until reaction is obtained at a temperature of between 100 and 200° C., preferably between 110 and 160° C., for a time of between 1 and 5 hours.

The isocyanate functional groups/amine functional groups ratio is between 2 and 50, preferably between 4 and 25.

Another alternative form of the process for the synthesis of polybiurets comprises reacting a compound comprising at least one isocyanate functional group with a compound carrying at least one alkoxydialkylsilane functional group and/or one alkyldialkoxysilane functional group and/or one trialkoxysilane functional group and at least one urea or thiourea functional group. The reaction medium is maintained at a temperature of between 100 and 200° C., preferably between 110 and 160° C., for a time of between 1 and 5 hours, in the optional presence of a catalyst chosen from carboxylic acids and/or Lewis acids.

The structures obtained can be written as follows:

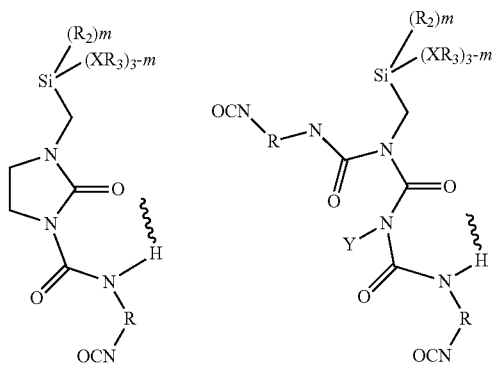

The compounds carrying at least one alkoxydialkylsilane functional group and/or one alkyldialkoxysilane functional group and/or one trialkoxysilane functional group and at least one urea functional group have the formulae:

$$(Y)_2-N-C(=Z)-N(-Y)-R_5-Si(R_3-X)_{3-m}(R_2)_m$$ or $$C(=Z)-[(NY-R_5-Si(R_3-X)_{3-m}(R_2)_m)]_2$$

with Y as defined above and at least one of the Y groups is equal to H, it being possible for Y to be an optionally substituted alkylene chain bridging the two nitrogens of the urea, $$A-N(Y)_d-C(=Z)-N(Y)-R_5-Si(R_3-X)_{3-m}(R_2)_m$$

with

A representing the residue of a hydrocarbon backbone comprising at least one primary or secondary amine functional group inserted in a urea or thiourea bond, with Y as defined above and at least one of the Y groups is equal to H, it being possible for Y to be an optionally substituted alkylene chain bridging the two nitrogens of the urea, Z=O or S.

Mention may be made, as nonlimiting examples of ureas, of aminocarbonyl amino 1 propyltrimethoxysilane, amino carbonyl amino 1 propyl triethoxysilane, N2(propyl trimethoxysilane) imidazolidin 1 one or N2(propyl triethoxysilane) imidazolidin 1 one.

The process for the synthesis of the polyacylurea biurets comprises
- adding, to the starting isocyanate or to the starting polyisocyanate mixture, a compound carrying at least one carboxylic acid functional group,
- raising the temperature to a value of approximately 100° C., plus or minus 20° C.,
- adding, to this reaction medium, a compound carrying at least one primary or secondary amine functional group and carrying at least one silane functional group, or a mixture of these amines,
- maintaining the reaction medium at a temperature of between 100 and 200° C., preferably between 110° C. and 160° C., for a time of between 1 and 5 hours,
- removing the unreacted monomer by a suitable process, such as vacuum distillation on a thin film device,
- recovering the polyacylurea biuret product comprising alkoxysilane units and comprising isocyanate units.

An alternative form of the process comprises adding the amine to the isocyanate and to the acid compound under cold conditions and subsequently heating to a temperature of between 100 and 200° C., preferably between 110° C. and 160° C., for a time of between 1 and 5 hours.

Another alternative form of the process comprises adding the isocyanate to the amine or to the amine carboxylate or mixture of amines comprising silane functional groups and raising the reaction temperature until reaction is obtained at a temperature of between 100 and 200° C., preferably between 110 and 160° C., for a time of between 1 and 5 hours.

The ratio of carboxyl functional groups to isocyanate functional groups at the start is between 1/20 and 1/4.

Generally, the NCO/nucleophiles (COOH+amines) ratio is between 1 and 50, preferably between 2 and 25.

The degree of conversion of the isocyanate monomers depends on the NCO/amines and NCO/COOH ratio. The greater the NCO/nucleophiles ratio, the lower the degree of conversion of isocyanate functional groups.

Surprisingly, in comparison with conventional biurets obtained from hexamethylene diisocyanate (HDI) and for comparable degrees of conversion of isocyanate functional groups, the compounds which are subject matter of the invention are characterized by a lower viscosity, which is an advantageous component in reducing the volatile organic compounds discharged to the atmosphere. Thus, some biurets obtained from HDI and 1 aminopropyltriethoxysilane exhibit a viscosity of 2570 mPa·s at 25° C. for a degree of conversion of the order of 45%, whereas HDI biurets result in viscosities of the order of 9000 mPa·s at 25° C. for comparable degrees of conversion.

The viscosity of the compounds which are subject matters of the invention very clearly depends on the isocyanate monomer used, aliphatic compounds giving generally higher viscosities than short-chain (4 to 10 chain members) aliphatic isocyanate derivatives.

The compounds of the invention obtained by the process are characterized by:
the presence of at least one biuret and/or acylurea bond,
and an NCO content of between 0 and 20% by weight of NCO per 100 g of solution, preferably of between 1 and 19%,
and a content of Si—X—$R_3$ units, expressed as % by weight of silicon (Si), of between 0.1% and 17.5%, preferably of between 0.5% and 13%, and an oligomeric distribution.

The compounds of the invention exhibit a twofold reactivity, the reactivity of the isocyanate functional groups and the reactivity of the alkoxysilane functional groups.

The compounds of the invention can thus exhibit very broad ranges of functionality according to the compounds involved and according to the NCO/nucleophiles (amine, urea, amides) ratio involved.

Thus, aminoalkyltrialkoxysilanes, monomeric compounds possessing three potentially reactive alkoxysilane functional groups (functionality 3), rapidly result in compounds having a high functionality. Thus, true biuret compounds of structure 1 and 2 exhibit a potential functionality of 5 (two isocyanate functional groups and three alkoxysilane functional groups).

The tris biuret comprising three biuret units will have a functionality of 11 (two isocyanate functional groups and 3×3 alkoxysilane functional groups).

It is thus difficult to calculate the mean functionality of the crosslinking composition insofar as each alkoxysilane group constitutes a potential site of reaction.

The compositions are characterized by a distribution composed of at least one of the following compounds:

mixed true biuret and/or mixed true acylurea compounds of the invention comprising at least one silane functional group devoid of free isocyanate functional group, and/or mixed true biuret and/or mixed true acylurea compounds of the invention comprising at least one silane functional group and at least one free isocyanate functional group, and/or polybiuret and/or acylurea compounds of the invention comprising at least one silane functional group devoid of free isocyanate functional group, and/or true polybiuret and/or true polyacylurea compounds of the invention comprising at least one silane functional group and at least one free isocyanate functional group.

Optionally, the composition comprises isocyanates or polyisocyanates not comprising silane units, namely:
starting mixture of isocyanates or isocyanate and alkyl carbamate compounds,
and optionally starting mixture of isocyanates or isocyanate and alkyl allophanate compounds,
isocyanate isocyanurate compounds,
biuret compounds.

The term "true biuret" is understood to mean the reaction product of two isocyanate functional groups with an amine functional group. The term "mixed true biuret" is understood to mean the preceding compound, the backbone of which carrying the amine functional group is different from the backbone of which carrying the isocyanate functional groups.

The compounds which are subject matters of the invention can be used for the synthesis of functional derivatives or the preparation of compositions for mastics or for coatings applied to organic or inorganic surfaces (metal, plastics, wood, cloth, leather, concrete, and the like) for decorative, functional and/or protective purposes, as coupling agents between a surface and a functional organic or inorganic compound.

The compounds of the present invention can also be incorporated in the manufacture of materials based on polyurethanes (foams), on elastomers, on fibers or on rubber.

The fields of application are thus very diverse (paints, varnishes, adhesives, tires, and the like) and relate just as well to interior applications as to exterior applications (exposed to natural light) or applications exposed to specific media (materials immersed in water, and the like).

These compounds can also be used to modify the surface properties of coatings (hydrophobization, hardness, and the like).

The compounds of the invention exhibit low coloring indices of less than 200 Hazen.

The isocyanate functional groups carried by the compounds of the invention of the final mixture can be definitively or temporarily and completely or partially functionalized by various nucleophilic components which can be chosen from:
alkoxysilanes comprising nucleophilic functional groups, such as, for example, amino- or thioalkyltrialkoxysilanes,
hydroxyalkyl acrylates,
chain extenders, such as diamines, diols or polyols,
agents for temporarily blocking the isocyanate functional groups which are well known to a person skilled in the art, such as oximes, pyrazoles, triazoles, imidazoles, lactams or ketoesters, it being possible for all these compounds to carry one or more substituents. Mention may thus be made, as nonlimiting examples, of methyl ethyl ketoxime, 3,5-dimethylpyrazole, ε-caprolactam, and the like.

Some of these derivatives constitute compounds possessing a twofold reactivity. Thus, mention may be made, as nonlimiting examples, of the compounds of the invention in which the isocyanate functional groups are blocked by a thermolabile temporary blocking agent and the compounds of the invention in which the isocyanate functional groups are functionalized by acrylate or methacrylate derivatives.

The compositions which are a subject matter of the invention can be used

- to react with the hydroxyl functional groups of polyol polymers, such as cellulose, guars or wood, in order to confer various properties, such as water repellency, thereon,
- to react with functional groups comprising a mobile hydrogen of polyols, such as the hydroxyl functional groups of a polyol polymer and/or the amine or thiol or carboxyl functional groups of polymers, in order to obtain polyurethane and/or polyurea and/or polythiourethane and/or polyamide coatings,
- as additives for coating, varnish or adhesive formulations, in order to contribute particular properties, such as, for example, the lowering of surface tension,
- to react with hydroxyl or silanol functional groups of inorganic compounds, such as silica or titanium dioxide or zirconia,
- to react with other silane compounds carrying at least one alkoxysilane functional group, such as epoxyalkyltrialkoxysilanes, alkyltrialkoxysilanes, tetraalkoxysilanes, and the like.

These compounds can be reacted in the organic phase or in the aqueous phase.

In the case of coatings of polyurethane or polyurea type, the coproducts of reaction with the compounds of the invention can be:

- acrylic poly(thi)ols derived from the polymerization of monomeric compounds carrying activated double bonds, such as (cyclo)alkyl or hydroxyalkyl acrylates or methacrylates,
- acrylic polyamines,
- polyester polyamine or poly(thi)ol polymers resulting from the polycondensation of a diacid or diester or carbonate with a diol or an aminoalcohol,
- polycarbonate poly(thi)ol polymers,
- polysiloxane compounds comprising alkyl units carrying hydroxyl and/or amino and/or thio functional groups polyamines,
- polyethers carrying hydroxyl and/or amine and/or thiol functional groups hydroxyl functional groups,
- polyprene compounds comprising hydroxyl or carboxylic acid functional groups,
- alkoxysilanes,
- or polymeric compounds comprising temporarily blocked hydroxyl, thiol or amine functional groups. Mention may be made, as examples of these blocked functional groups, of imines, dioxolanes, acetals, and the like.

The synthesis of these polymers and the constituent monomers of these polymers are widely known to a person skilled in the art. Mention may be made, as examples of monomers carrying double bonds, of n-butyl, cyclohexyl, methyl, isopropyl or tert-butyl acrylates and methacrylates, acrylamide and methacrylamide as well as their N-alkylated derivatives, acrylic acid and methacrylic acid, styrene, butadiene or vinyl derivatives.

Mention may be made, as nonlimiting examples of monomers of the polycondensation reaction, of adipic acid, succinic acid, glutaric acid, dodecanedioic acid, phthalic acid, esters of these diacids, alkylene carbonates, such as methylcarbonate, ethylcarbonate, propylenecarbonate or ethylenecarbonate, or diols, such as butanediols, hexanediols, cyclohexanediols, and the like.

Mention may be made, as examples of polyether compounds or epoxy polymers, of ethylene oxide or propylene oxide.

Compounds such as various fillers, catalysts, rheology additives or pigments can be added to the formulations in order to introduce the desired properties.

The following examples are representative of the invention.

Analytical Methods and Definitions:

A compound comprising a mobile hydrogen, the addition compound of which with a linear aliphatic isocyanate functional group exhibits a release temperature at most equal to 180° C., is regarded as a blocking agent.

Test with Octanol—Definitions

| | |
|---|---|
| "Release" (or "unblocking") temperature: | This is the lowest temperature at which the blocking agent of the blocked isocyanate is displaced to a level of 9/10 (mathematically rounded) by a primary monoalcohol (the primary alcohol is generally octanol). |
| Lifetime on storage: | To ensure a good lifetime on storage, it is preferable to choose blocked isocyanate functional groups for which the test with octanol shows a "release" at 80° C., advantageously at 90° C., at most equal to 90%. |
| Progress of the reaction: | The reaction is regarded as complete if it is carried out to more than 90%. |

Procedure

Approximately 5 mmol as protected blocked NCO equivalent to be evaluated are charged to a tube of Schott type with magnetic stirring.

2.5 to 3 ml of 1,2-dichlorobenzene (solvent) and the equivalent of 1-octanol (5 mmol, i.e. 0.61 g and optionally with the catalyst to be tested with the blocking group) are added.

The reaction medium is subsequently brought to the test temperature. Heating is then carried out at the test temperature for 6 h, so as to deblock and thus render reactive the isocyanate functional groups. On completion of the reaction, the solvent is removed by vacuum distillation and the residue is analyzed by NMR, mass and infrared spectroscopy.

From these data, the percentage of blocked isocyanate functional group condensed with the 1-octanol is evaluated.

Quantitative Determination of the Isocyanate Functional Groups:

The standardized method for the quantitative determination of isocyanate functional groups by the "dibutylamine" method is used. Back titration by a standard HCl solution of the N,N-dibutylamine not consumed by the reaction with the isocyanate functional groups of the mixture to be quantitatively determined. The difference between the N,N-dibutylamine which is reacted and the amount introduced makes it possible to measure the content of isocyanate functional groups of the mixture to be quantitatively determined.

Determination of the Mn and Mw Values of the Polymers:

Gel permeation chromatography is used as method for determining the number-average and weight-average molecular weights. Polystyrene standards of known molecular weight are used to calibrate the gel permeation columns. The elution solvent used is a good solvent for the standard polymers and for the polymers to be analyzed. It is chosen taking into account the constraints introduced by the method for the detection of the polymers (refractometry or analysis by ultraviolet absorption or analysis by infrared). This solvent is chosen from ethers, such as tetrahydrofuran, chlorinated derivatives, such as dichloromethane, and the like.

The elution volume of the polymers to be analyzed is compared with the elution volumes of the standard polymers and the molecular weight is thus deduced therefrom. The constituent oligomers eluted of the mixture to be analyzed can also be recovered separately for analysis and characterization by various structural analytical techniques, such as $^1$H NMR, $^{13}$C NMR, infrared, and the like.

ABBREVIATIONS USED

HDI: hexamethylene diisocyanate

GPC: gel permeation chromatography

DBA: N,N-dibutylamine

APTEO: aminopropyltriethoxysilane

APTMO: aminopropyltrimethoxysilane

SYNTHETIC EXAMPLES

Example 1

Biuret of Hexamethylene Diisocyanate (HDI) and of Aminopropyltriethoxysilane (APTEO) (CMI 1487)

1680 g of hexamethylene diisocyanate are introduced into a 3 l reactor equipped with a mechanical stirrer, dropping funnels and a reflux condenser and rendered inert with nitrogen. The starting NCO content is 1.19. The temperature of the reaction medium is 18.5° C. 456.5 g of aminopropyltriethoxysilane (APTEO) are then added over one hour. The NCO/amine molar ratio is 10/1. An exothermal drift and the appearance of a white precipitate in the reaction medium are observed. The exothermic reaction is taken advantage of in raising the temperature of the reaction medium to 100° C. The temperature of the reaction medium thus gradually rises: at the end of 10 minutes after the addition, the temperature of the reaction medium is 25° C., 43° C. after 30 minutes and 93° C. after 55 minutes. At the end of one hour, the precipitate observed is virtually entirely soluble in the reaction medium. From the end of the addition, the temperature of the reaction medium is raised to 140° C. by contributing external energy. After reacting for two hours at 140° C., the content of isocyanate functional groups of the reaction medium is 0.729 mol of NCO per 100 g of reaction medium.

The reaction medium is then purified by 2 successive distillations of the HDI monomer on a thin film device under a vacuum of 0.4 mbar and at 160° C. with a throughput of 900 g/hour for the first pass and 250 g/hour for the second pass.

960 g of a composition formed of biuret of hexamethylene diisocyanate (HDI) and of aminopropyltriethoxysilane (APTEO) are recovered, i.e. a yield of the order of 45%.

The NCO content is 0.364 (i.e., approximately 15.3%) and the viscosity is 2575 mPa·s at 25° C.

The silicon content is 3% by weight.

The proton NMR analysis in CDCl$_3$ medium gives the following distribution of the functional groups:

| Units | Moles of units | % by weight of units |
|---|---|---|
| Sum of the HDI units | 100 | 74.4 |
| including carbamate | 1.3 | 1.4 |
| including allophanate | 0.3 | 0.5 |
| (EtO)$_3$Si(CH$_2$)$_3$—N— unit | 26 | 23.6 |

The distribution of the biuret units is as follows and is measured with regard to the following signals of the NH groups (at 7.5, 7.0 and 6.7 ppm).

| Units | Chemical shift | % |
|---|---|---|
| HDI/(EtO)$_3$Si(CH$_2$)$_3$—N— mixed biuret | 7.5 ppm | 49 |
| True HDI biuret | 7.0 ppm | 39 |
| Urea | 6.7 ppm | 12 |

The true HDI biuret unit is composed of three hexamethylene chains bonded to the biuret unit via the nitrogens.

The mixed biuret is composed of two hexamethylene chains of the HDI and of a propyltriethoxysilane chain which are bonded to the biuret unit via the nitrogens.

A composition is thus obtained which is composed of biuret isocyanate oligomers with different degrees of polymerization composed of HDI and APTEO biuret oligomeric compounds, of true HDI biuret oligomers and of compounds composed of a sequence of true HDI biuret and of HDI and APTEO biuret.

The functionality of isocyanate functional group is thus slightly greater than 3 insofar as, during the process, there was formation of true HDI biuret, which is trifunctional.

Example 2

Biuret of Hexamethylene Diisocyanate (HDI) and of Aminopropyltrimethoxysilane (APTMO) (CMI 1489)

The procedure is as for example 1, except that APTMO is used instead and in place of APTEO.

An NCO/NH$_2$ molar ratio of 10 is used. 1680 g of HDI and 370 g of APTMO are used.

The viscosity of the final composition after distillation of HDI is 3980 mPa·s at 25° C. and the NCO content is 0.356, i.e. 15%. The silicon content is 3.8%.

The yield recovered is 45%, i.e. 924 g of final composition, which exhibits the following characteristics.

The proton NMR analysis in CDCl$_3$ medium gives the following distribution of the functional groups:

| Units | Moles of units | % by weight of units |
|---|---|---|
| Sum of the HDI units | 100 | 70.2 |
| including carbamate | 4.2 | 4 |
| including allophanate | 0.7 | 1.2 |
| (EtO)$_3$Si(CH$_2$)$_3$—N—unit | 28.7 | 24.6 |

The distribution of the biuret units is as follows and is measured with regard to the following signals of the NH groups (at 7.5, 7.0 and 6.7 ppm).

| Units | Chemical shift | % |
|---|---|---|
| HDI/(EtO)$_3$Si(CH$_2$)$_3$—N—mixed biuret | 7.5 ppm | 59 |
| True HDI biuret | 7.0 ppm | 30 |
| Urea | 6.7 ppm | 11 |

Example 3

Biuret of Hexamethylene Diisocyanate (HDI) and of Aminopropyltrimethoxysilane (APTMO) (CMI 1539)

The procedure is as for example 2 with regard to the same amounts of products but slightly modifying the operating conditions; in particular, the heating time is 3 h instead of 2 h.

927 g of product, i.e. a yield of 45%, are obtained, with an NCO content of 0.342, i.e. 14.4%, and with a viscosity of 5420 mPa·s at 25° C. The silicon content is 3.5%.

It is found that the process is reproducible.

Example 4

Biuret of Hexamethylene Diisocyanate (HDI) and of Aminopropyltrimethoxysilane (APTMO) (CMI 1478)

The procedure is as for examples 2 and 3, except that the batch is separated into two before distillation of the monomer. 1010 g of product are purified by distillation of the HDI monomer.

430 g of product, i.e. a yield of 42.55%, are obtained, with an NCO content of 0.347, i.e. 14.6%, and with a viscosity of 5090 mPa·s at 25° C. The silicon content is 2.5%.

The proton NMR analysis in CDCl$_3$ medium gives the following distribution of the functional groups:

| Units | Moles of units | % by weight of units |
|---|---|---|
| Sum of the HDI units | 100 | 70.5 |
| including HDI and monomethyl carbamate | 2.7 | 2.2 |
| including HDI and methyl allophanate | 0.6 | 0.9 |
| (EtO)$_3$Si(CH$_2$)$_3$—N—unit | 29.7 | 25.5 |

The distribution of the biuret units measured with regard to the following signals of the NH groups (7.5, 7.0 and 6.7 ppm) is as follows:

| Units | Chemical shift | % |
|---|---|---|
| HDI/(EtO)$_3$Si(CH$_2$)$_3$—N—mixed biuret | 7.5 ppm | 63 |
| True HDI biuret | 7.0 ppm | 28 |
| Urea | 6.7 ppm | 9 |

The analysis of the oligomeric distribution by gel permeation gives the following distribution:

| Entities | % by weight |
|---|---|
| HDI monomer and NCO-propyltrimethoxysilane | 0.2 |
| HDI and monomethyl carbamate | 0.4 |
| True HDI dimer | 1 |
| HDI and monomethyl allophanate | 0.6 |
| True 2 HDI/1 (EtO)$_3$Si(CH$_2$)$_3$—NH—mixed biuret | 37.4 |
| HDI-true 2 HDI/1 (EtO)$_3$Si(CH$_2$)$_3$—NH—mixed biuret dimer | 1.8 |
| Mixed (3 HDI-2 (EtO)$_3$Si(CH$_2$)$_3$—NH—) bis biuret | 23.2 |
| Mixed (4 HDI-3 (EtO)$_3$Si(CH$_2$)$_3$—NH—) tris biuret + true HDI biuret sequence | 16 |
| Mixed (4 HDI-3 (EtO)$_3$Si(CH$_2$)$_3$—NH—) heavy biuret + true HDI biuret sequence | 19.4 |

Example 5

Biuret of Hexamethylene Diisocyanate (HDI) and of Aminopropyltriethoxysilane (APEMO) (CMI 1460)

The procedure is as for example 1, except that the NCO/NH$_2$ ratio is 7.

765 g of HDI and 287 g of APETO are employed.

After purification, 571 g are obtained, i.e. a yield of 55%.

The NCO content is 0.317, i.e. 13.3%, and the viscosity is 6790 mPa·s at 25° C. The silicon content is 3.5%.

The analysis of the oligomeric distribution is presented in the table below.

| | 02CMI146002 foot |
|---|---|
| HDI | <0.1 |
| HDI and ethyl carbamate | 0.3 |
| True HDI dimer (trace of carbamate) | 0.5 |
| Mixed biuret (trace of trimer functional group) | 30.0 |
| Mixed bis biuret (trace of dimer and trimer functional group) | 24.1 |
| Mixed tris biuret (trace of dimer and trimer functional group) | 16.5 |
| Heavy product (mixed tetra biuret) (trace of dimer and trimer functional group) | 28.6 |

Example 6

Biuret of Hexamethylene Diisocyanate (HDI) and of Aminopropyltriethoxysilane (APEMO) (CMI 1459)

The procedure is as for example 1, except that the NCO/NH$_2$ ratio is 10.

840 g of HDI and 221 g of APETO are employed.

After purification, 466 g are obtained, i.e. a yield of 44%.

The NCO content is 0.359, i.e. 15%, and the viscosity is 2850 mPa·s at 25° C. The silicon content is 3.35%.

The process is reproducible.

The analysis of the composition is presented in the table below.

| Entities | 02CMI145902 foot |
|---|---|
| HDI | <0.1 |
| HDI and ethyl carbamate | 0.3 |
| True HDI dimer | 1.2 |
| Mixed biuret (trace of trimer functional group) | 38.4 |
| Mixed bis biuret (trace of dimer and trimer functional group) | 27.0 |
| Mixed tris biuret (trace of dimer and trimer functional group) | 14.9 |
| Heavy product (mixed tetra biuret) (trace of dimer and trimer functional group) | 18.2 |

Example 7

Composition Formed of Polybiuret and Polyisocyanurate Comprising Trialkoxysilane Functional Group (CMI 1479)

1010 g of composition from example 4 are introduced into a 3 l reactor equipped with a mechanical stirrer, dropping funnels and a reflux condenser and rendered inert with nitrogen. The NCO content of the reaction medium is 30% (0.716 NCO per 100 g). The reaction medium is brought to 110° C. and 10 g of hexamethyldisilazane (10% by weight) are introduced with stirring. The temperature of the reaction medium is brought to 140° C. over 50 minutes and this temperature is maintained for 3 hours. The degree of conversion of the NCO functional groups is regularly measured. It changes as follows: 8.9% at the end of 1 hour of reaction after addition of HMDZ, 10.6% after 1 h 30, 14.8% after 2 h 30 and 16.8% after 3 hours. The reaction medium is cooled to 100° C. over 25 minutes and 4.6 g of 1-butanol are added to the reaction medium in order to halt the cyclotrimerization reaction. The reaction medium is subsequently purified to remove the excess monomer. The same purification method as that described in example 1 is used.

484 g of composition formed of polybiuret polyisocyanurate comprising alkoxysilane units are obtained, i.e. a yield of 47%.

The NCO content is 0.369, i.e. 15.5% by weight. The viscosity is 11 800 mPa·s at 25° C.

The oligomeric distribution of the composition thus obtained is presented below.

| Entities | % by weight |
|---|---|
| HDI monomer and NCO-propyltrimethoxysilane | 0.2 |
| HDI and monomethyl carbamate | 0.4 |
| Isocyanatopropyltrialkoxysilane and monomethyl carbamate | 0.3 |
| True HDI dimer | 1.8 |
| HDI and monomethyl allophanate | 2 |
| Mixture of true 2 HDI/1 (EtO)$_3$Si(CH$_2$)$_3$—NH— mixed biuret and of true isocyanurate trimer of HDI and of true isocyanurate trimer of HDI and of isocyanato-propyltrialkoxysilane | 32.3 |
| HDI-true 2 HDI/1 (EtO)$_3$Si(CH$_2$)$_3$—NH— mixed biuret dimer | 3.7 |
| Mixed (3 HDI-2 (EtO)$_3$Si(CH$_2$)$_3$—NH—) bis biuret and mixed (3 HDI-2 (EtO)$_3$Si(CH$_2$)$_3$—NH—) biuret - and comprising isocyanurate and dimer units | 19.3 |
| Heavy products composed of mixed (4 HDI-3 (EtO)$_3$Si(CH$_2$)$_3$—NH—) biuret and true HDI biuret sequences and comprising isocyanurate, dimer, carbamate and allophanate units* | 40 |

*see below an example of structures formed of sequences comprising biuret and isocyanurate units comprising alkoxysilane units.

The proton NMR analysis in CDCl$_3$ medium gives the following distribution of the functional groups:

| Units | Moles of units | % by weight of units |
|---|---|---|
| Sum of the HDI units | 100 | 70.2 |
| including HDI and monomethyl carbamate | 4.5 | 3.7 |
| including HDI and methyl allophanate | 2.9 | 4.5 |
| including HDI isocyanurate units | 8.4 | 5.9 |
| (EtO)$_3$Si(CH$_2$)$_3$—N— unit | 16.8 | 14.4 |
| Sum of the units resulting from the butanol (carbamate allophanate) | 3.6 | 1.1 |

The distribution of the biuret units, measured with regard to the following signals of the NH groups (7.5, 7.0 and 6.7 ppm), is as follows:

| Units | Chemical shift | % |
|---|---|---|
| HDI/(EtO)$_3$Si(CH$_2$)$_3$—N— mixed biuret | 7.5 ppm | 39 |
| True HDI biuret | 7.0 ppm | 50 |
| Urea | 6.7 ppm | 11 |

Nonlimiting example of structures formed of sequences comprising biuret and isocyanurate units comprising alkoxysilane units

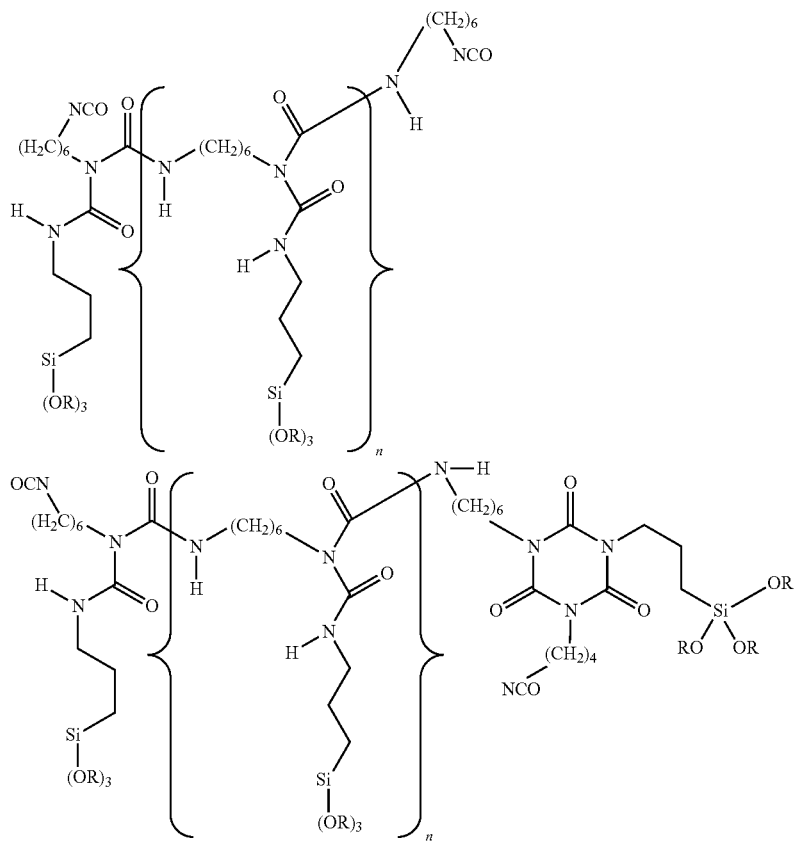

Examples 8 to 10

Examples of the Functionalization of the Silane Biuret Compounds

Example 8

Polyurethane Polydimethylsiloxane Polybiuret Prepolymer Comprising Trialkoxysilane Functional Groups (CMI 1488)

100 g of a composition of example 1 and 182 g of a telechelic silicone oil comprising 2 hydroxypropyl functional groups (Rhodorsil V75) are charged to a reactor. The content of isocyanate functional groups is 0.129.

The NCO functional groups/OH functional groups molar ratio is 2.

The mixture is heated to 80° C. and the content of isocyanate functional groups is monitored. It changes in the following way:
- after reacting for 2 h 40, the content is 0.113, i.e. a consumption of NCO functional groups of 12.4%,
- after reacting for 4 h, the content is 0.097, i.e. a consumption of NCO functional groups of 24.8%,
- after reacting for 9 h at 80° C., the NCO content is 0.066 (2.77%), i.e. a degree of conversion of 49%.

A composition formed of polyurethane polydimethylsiloxane polybiuret prepolymer comprising pendant trialkoxysilane functional groups with an NCO content of 2.77% is thus obtained. The product is a viscous liquid.

This product is used as adhesion primer for silicone mastics.

Example 9

Polyurethane Polybiuret Comprising Trialkoxysilane Functional Groups (CMI 1491)

The isocyanate functional groups of a compound of example 2 are blocked by methanol in order to obtain the corresponding methyl carbamate.

100 g of a composition of example 2 and 11.5 g of methanol are introduced into a reactor. The NCO content is 3.320 and the NCO/OH ratio is 1.

The mixture is heated at 60° C. for 4 h. The NCO content measured is 0.055. After a further 6 h at 80° C., the NCO content is 0.017 mol of NCO per 100 g, i.e. 0.71%.

A composition formed of polybiuret comprising trialkoxysilane functional groups polymethyl carbamate is obtained.

These compounds can be used to be crosslinked with melamines and make possible better attachment of the pigments to the network thus obtained.

Example 10

Polyurea Polybiuret Comprising Mixed Trialkoxysilane Functional Groups (CMI 1491)

100 g of example 1 are charged to a reactor and then 67.3 g of aminopropyltrimethoxysilane are added over 15 minutes. The NCO/NH$_2$ ratio is equal to 1. The content of NCO functional group is 0.218.

The reaction is exothermic and the temperature of the reaction medium rises to 100° C. After reacting at 80° C. for 3 hours, the content of NCO functional groups is 0.

The reaction mass is subsequently withdrawn at 100° C. After cooling, the composition obtained gives a nonsticky off-white paste.

Example 11

Polybiuret Comprising Mixed Trialkoxysilane Functional Groups and Comprising Acrylic Units and Comprising Isocyanate Functional Groups which are Free (CMI 1491)

This composition is a composition of use for systems comprising a threefold crosslinking system:
- crosslinking via isocyanate functional groups with polyol or polyamine compounds comprising a mobile hydrogen,
- crosslinking by a radiative technique (crosslinking under UV radiation or electron gun) with other crosslinkable monomers possessing double bonds,
- crosslinking with silanol or hydroxyl functional groups of inorganic materials (silica, titanium dioxide, zirconia) or alkoxysilanes.

These systems are therefore advantageous for acting as coupling agents between an inorganic material and an organic material.

100 g of composition of example 1 (NCO content of 0.364 mol of NCO per 100 g), 14.1 g of hydroxyethyl acrylate (HEA), i.e. 0.121 mol, and 114 mg of BHT (2,6-bis(tert-butyl)-4-methylphenol, i.e. 1000 ppm with respect to HEA) are introduced into a reactor.

The mixture is heated at 80° C. for 12 hours.

The NCO content is measured and changes as follows:
- after 2 h 30, the NCO content is 0.266, i.e. a degree of conversion of NCO of 16.6%,
- after 4 h 30, the NCO content is 0.239, i.e. a degree of conversion of NCO of 25.1%,
- after 6 h, the NCO content is 0.227, i.e. a degree of conversion of NCO of 29%,
- after 11 h, the NCO content is 0.219, i.e. a degree of conversion of NCO of 31.3%,
- after 12 h, the NCO content is 0.215, i.e. a degree of conversion of NCO of 32.6%.

The calculated theoretical NCO content is 0.213 mol of NCO per 100 g.

The reaction is thus halted and the composition thus obtained is a liquid composition which exhibits a content of NCO functional group of 9% and a silicon content of 2.6%.

One of the compounds of the composition obtained can thus be written as follows:

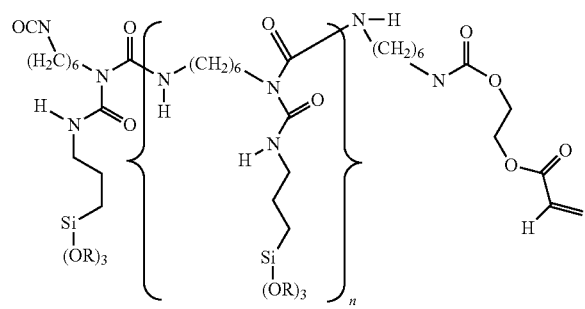

Comparative Example 1

100 g of Tolonate HDT (HDI polyisocyanurate sold by Rhodia) with a content of NCO functional groups of 0.52 mol per 100 g are introduced into a reactor equipped as in example 1. 115 g of aminopropyltriethoxysilane (i.e. 0.52 mol) are run in over 1 hour. The NCO/NH$_2$ ratio is 1.

An immediate precipitation of urea formed from Tolonate HDT and from aminopropyltriethoxysilane is observed, with release of a considerable amount of heat. The mixture becomes difficult to stir.

The product is a solid which is difficult to handle and which is not very soluble in organic solvents, such as Solvesso or esters.

Comparative Example 2

The procedure is as for comparative example 1, except that aminopropyltrimethoxysilane (93 g) is used as silane. Compounds are thus obtained which precipitate and which are sparingly soluble in organic solvents.

Applicational Results Obtained with the Compounds of the Invention

The compounds of the invention have been used with success in 4 fields of application:
- coatings, paints and varnishes,
- silicone mastics and adhesion primers on various surfaces,
- heavy-weight tires,
- polyamide fiber coatings.

Structure 7 on column 13, lines 50-59 (one skilled in the art would recognize that "=OMe" in the structure should read "=O") should be shown as:
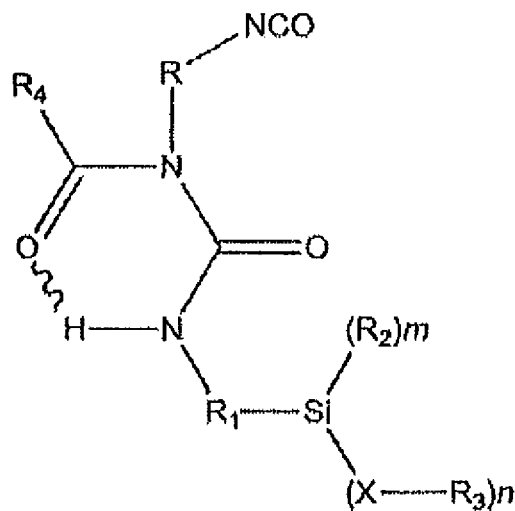

What is claimed is:

1. A process for the preparation of an isocyanate composition comprising biuret functional groups, comprising the steps of (a) reacting at least one isocyanate monomer with an aminoalkylsilane to form an isocyanatoalkylsilane and (b) reacting the isocyanatoalkylsilane with an isocyanate to form a biuret,
where the amino portion of the aminoalkylsilane unit in the isocyanate composition is an amino group of the biuret.

2. The process as claimed in claim 1, wherein at least 5% of biuret functional groups not carrying a silanoalkyl chain are formed with respect to the combined biuret functional groups in the composition.

3. The process as claimed in claim 1, wherein, expressed as equivalents, the ratio of the isocyanate functional groups to the number of hydrogens carried by the amine functional groups is at least 4.

4. The process as claimed in claim 1, wherein at least 10% of biuret functional groups not carrying a silanoalkyl chain are formed with respect to the combined biuret functional groups.

5. The process as claimed in claim 1, wherein, expressed as equivalents, the ratio of the isocyanate functional groups to the number of hydrogens carried by the amine functional groups is at least 8.

* * * * *

UNITED STATES PATENT AND TRADEMARK OFFICE
CERTIFICATE OF CORRECTION

PATENT NO. : 7,875,693 B2
APPLICATION NO. : 10/579808
DATED : January 25, 2011
INVENTOR(S) : Jean-Marie Bernard, Johannes Schwarz and Denis Revelant Page 1 of 2

It is certified that error appears in the above-identified patent and that said Letters Patent is hereby corrected as shown below:

Structures 7 and 8 on column 13, lines 50-65 should be shown as:

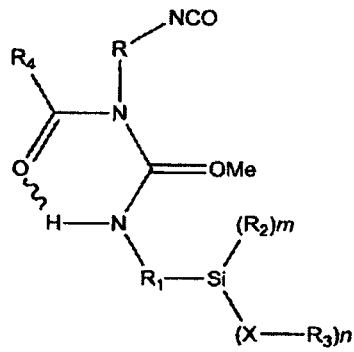

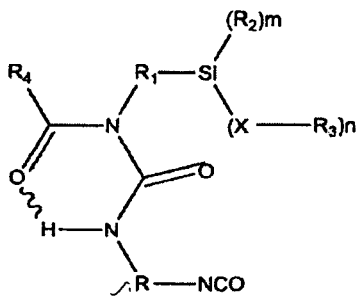

Structure 9 on column 14, lines 29-37 should be shown as:

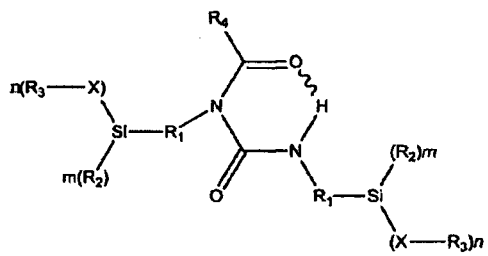

Signed and Sealed this
Thirteenth Day of September, 2011

David J. Kappos
*Director of the United States Patent and Trademark Office*

CERTIFICATE OF CORRECTION (continued)
U.S. Pat. No. 7,875,693 B2

Structure 10 on column 14, lines 29-37 should be shown as:

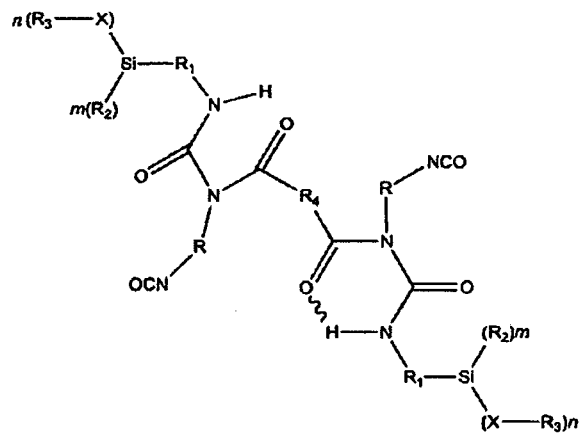

UNITED STATES PATENT AND TRADEMARK OFFICE
CERTIFICATE OF CORRECTION

| | | |
|---|---|---|
| PATENT NO. | : 7,875,693 B2 | Page 1 of 2 |
| APPLICATION NO. | : 10/579808 | |
| DATED | : January 25, 2011 | |
| INVENTOR(S) | : Jean-Marie Bernard et al. | |

It is certified that error appears in the above-identified patent and that said Letters Patent is hereby corrected as shown below:

Structure 5 on column 13, lines 2-25 (there are two "N-"s in the "q" parenthesis in the printed patent which is not the same as that shown on page 22 of the specification) should be shown as:

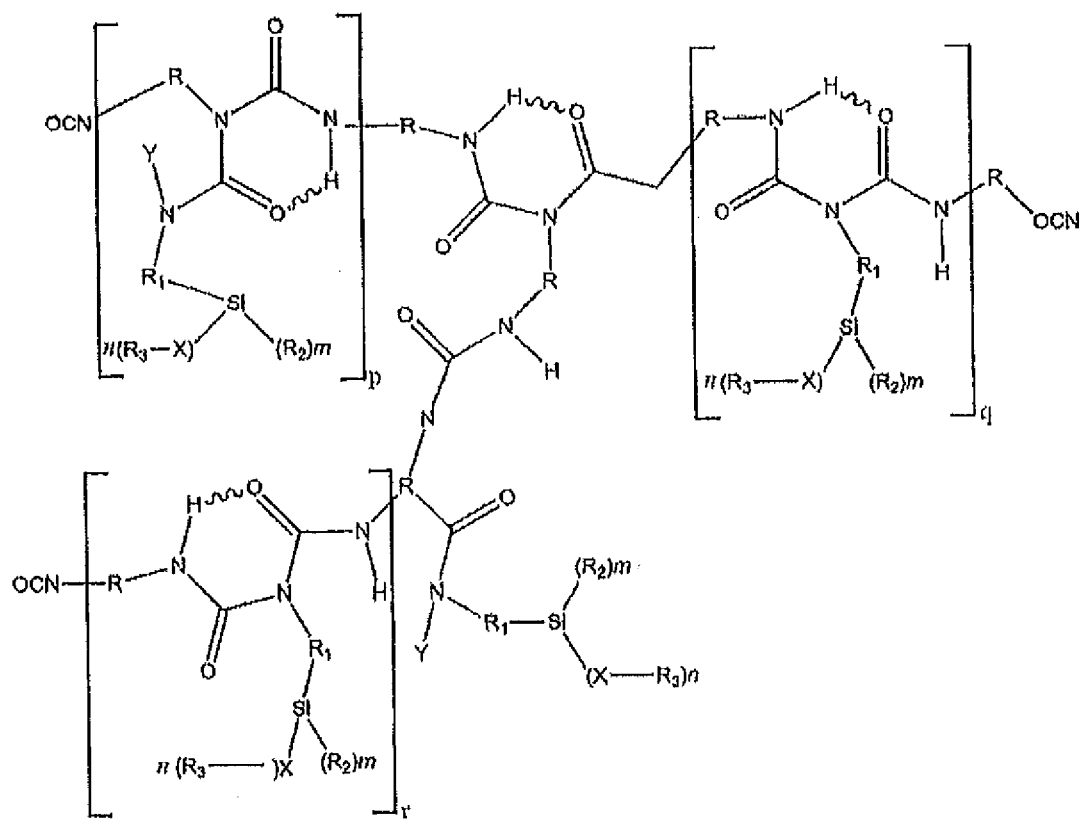

Signed and Sealed this
Twentieth Day of March, 2012

David J. Kappos
*Director of the United States Patent and Trademark Office*